United States Patent
Majumder

(10) Patent No.: US 9,126,883 B2
(45) Date of Patent: Sep. 8, 2015

(54) RECYCLE OF REACTOR EFFLUENT IN AN ALKYLAROMATIC PROCESS

(71) Applicant: UOP LLC, Des Plaines, IL (US)

(72) Inventor: Debarshi Majumder, Forest Park, IL (US)

(73) Assignee: UOP LLC, Des Plaines, IL (US)

( * ) Notice: Subject to any disclaimer, the term of this patent is extended or adjusted under 35 U.S.C. 154(b) by 261 days.

(21) Appl. No.: 13/923,125

(22) Filed: Jun. 20, 2013

(65) Prior Publication Data

US 2014/0378724 A1    Dec. 25, 2014

(51) Int. Cl.
*C07C 2/60* (2006.01)
*C07C 6/12* (2006.01)
*C07C 2/66* (2006.01)

(52) U.S. Cl.
CPC . *C07C 2/66* (2013.01); *C07C 6/126* (2013.01); *C07C 2529/08* (2013.01); *C07C 2529/70* (2013.01); *C07C 2529/80* (2013.01)

(58) Field of Classification Search
USPC .................. 585/467, 475, 323, 455
See application file for complete search history.

(56) References Cited

U.S. PATENT DOCUMENTS

| | | | |
|---|---|---|---|
| 4,870,222 A * | 9/1989 | Bakas et al. | 585/323 |
| 5,245,090 A | 9/1993 | DeCaria et al. | |
| 5,358,646 A | 10/1994 | Gloyna et al. | |
| 7,008,914 B2 | 3/2006 | Smith et al. | |
| 7,339,088 B1 | 3/2008 | O'Brien et al. | |
| 7,576,247 B2 | 8/2009 | Sohn et al. | |
| 7,632,473 B2 | 12/2009 | Sohn et al. | |
| 7,642,389 B2 | 1/2010 | Sohn et al. | |
| 7,652,182 B2 | 1/2010 | Sohn et al. | |
| 7,863,492 B2 | 1/2011 | Koper et al. | |
| 7,897,829 B2 | 3/2011 | Glover et al. | |
| 8,350,110 B2 | 1/2013 | Sohn et al. | |
| 8,389,787 B1 | 3/2013 | Majumder et al. | |
| 2004/0176654 A1 | 9/2004 | Abazajian | |
| 2008/0161617 A1 | 7/2008 | Riley | |

* cited by examiner

*Primary Examiner* — Thuan D Dang

(57) ABSTRACT

A method of making alkylaromatics is described. The process includes recycling a portion of the alkylation reaction zone effluent back to the alkylation zone to maintain the product quality while reducing energy usage.

8 Claims, 2 Drawing Sheets

RECYCLE OF REACTOR EFFLUENT IN AN ALKYLAROMATIC PROCESS

BACKGROUND OF THE INVENTION

Linear alkylbenzenes (LAB) are compounds that have significant commercial importance. Linear alkylbenzene sulfonate (LAS) compounds made by sulfonation of linear alkylbenzene are used in the manufacture of detergents and other products. Because linear alkylbenzenes are more easily biodegradable than branched alkylbenzenes, linear alkylbenzenes have essentially replaced branched alkylbenzenes in detergents and other products. In particular, linear alkylbenzenes with long alkyl chains, such as chains having about 10 to about 14 carbons, are commonly used. However, linear alkylbenzenes with longer chains and with shorter chains also are commercially important.

Linear alkylbenzenes often are made by alkylation of benzene with olefins. Positional isomers, such as 2-phenyl, 3-phenyl, 4-phenyl, 5-phenyl, and the like, result from this alkylation of benzene with long chain olefins. The distribution of the phenyl along the alkyl chain produces different products.

Historically, linear alkylbenzenes have been manufactured commercially using Friedel-Crafts condensation employing catalysts such as aluminum chloride, or by using strong acid catalysts such as hydrogen fluoride, for example, to alkylate benzene with olefins. In 1995, a solid bed alkylation process, the Detal™ process, using a solid non-corrosive acid catalyst was introduced.

Linear alkylbenzenes with a high percentage of the 2-phenyl isomer are highly desired because, when sulfonated, such compounds have long tails that provide enhanced solubility and detergent properties.

The 2-phenyl isomer content of the product is process dependent. Solid alkylation catalysts, such as those used in the Detal™ process, produce products with 2-phenyl isomer content between 25 and 35 percent. HF-catalyzed processes typically yield a 2-phenyl isomer content less than 20 percent, and $AlCl_3$ typically yield between 30 and 33 percent. The properties of linear alkylbenzenes and linear alkylbenzene sulfonate produced from these three processes have been disclosed by Berna and coworkers in the following publications. Journal of Surfactants and Detergents, Vol. 3, No. 2 (July 2000) pages 353 through 359, JAOCS, Vol. 72, No. 1 (1995) pages 115 through 122, and Tenside Surfactants Detergents 25 (1988) 4, pages 216 through 221.

Current LAB manufacturing processes employing solid alkylation catalysts use kerosene-based $C_9$ to $C_{16}$ material from a Pacol™ dehydrogenation process, which is typically a mixture of about 9-15% olefins in paraffin.

Gas-to-liquid (GTL) technologies for the generation of $C_9$ to $C_{16}$ range of hydrocarbons have raised interest in the possibility of producing LAB using a GTL-based feed source. The ability to use a GTL feedstock would reduce dependence on crude-based feedstocks.

Thus, there exists a need for additional methods for making linear alkylaromatics by alkylating aromatic compounds with olefins.

SUMMARY OF THE INVENTION

One aspect of the invention is a process for preparing linear alkylaromatics by the alkylation of an aromatic compound with olefins having between about 8 and 20 carbon atoms. In one embodiment, the process involves contacting the aromatic compound and a feed comprising a mixture of about 12 to about 30% olefins and about 70 to about 88% other components in an alkylation zone under alkylation conditions including a catalytically effective amount of a catalyst to provide an alkylation product containing alkylaromatics, dialkylaromatics, unreacted aromatic compound, and unreacted other components. The alkylation product is divided into a first portion and a second portion. The first portion of the alkylation product is recycled to the alkylation zone. The second portion of the alkylation product is separated into an aromatic-rich fraction containing the unreacted aromatic compound and a substantially aromatic compound-free fraction containing alkylaromatics, unreacted other components, and dialkylaromatics. The substantially aromatic compound-free fraction is separated into an other component-rich fraction containing the unreacted other components and a substantially other component-free fraction containing the alkylaromatics, and dialkylaromatics. The substantially other component-free fraction is separated into an alkylaromatic fraction containing the linear alkylaromatics and a heavies fraction containing the dialkylaromatics.

DETAILED DESCRIPTION OF THE INVENTION

Alkylbenzenes, also known as phenyl alkanes, are important for many different products. When the alkyl group has 8 to 20 carbon atoms, among the common usages is in the formation of detergents. Alkylbenzenes are an intermediate product used to form alkylbenzene sulfonates, which are surfactants that form the basis of many detergents. The alkylbenzene sulfonates are known to exhibit different physical properties based upon the position of the aromatic group on the alkyl chain. In the production of alkylbenzene sulfonates, the intermediate product alkylbenzenes with 2-phenyl isomer content in the range from about 30 to 40 percent are particularly desired.

Figure 1:
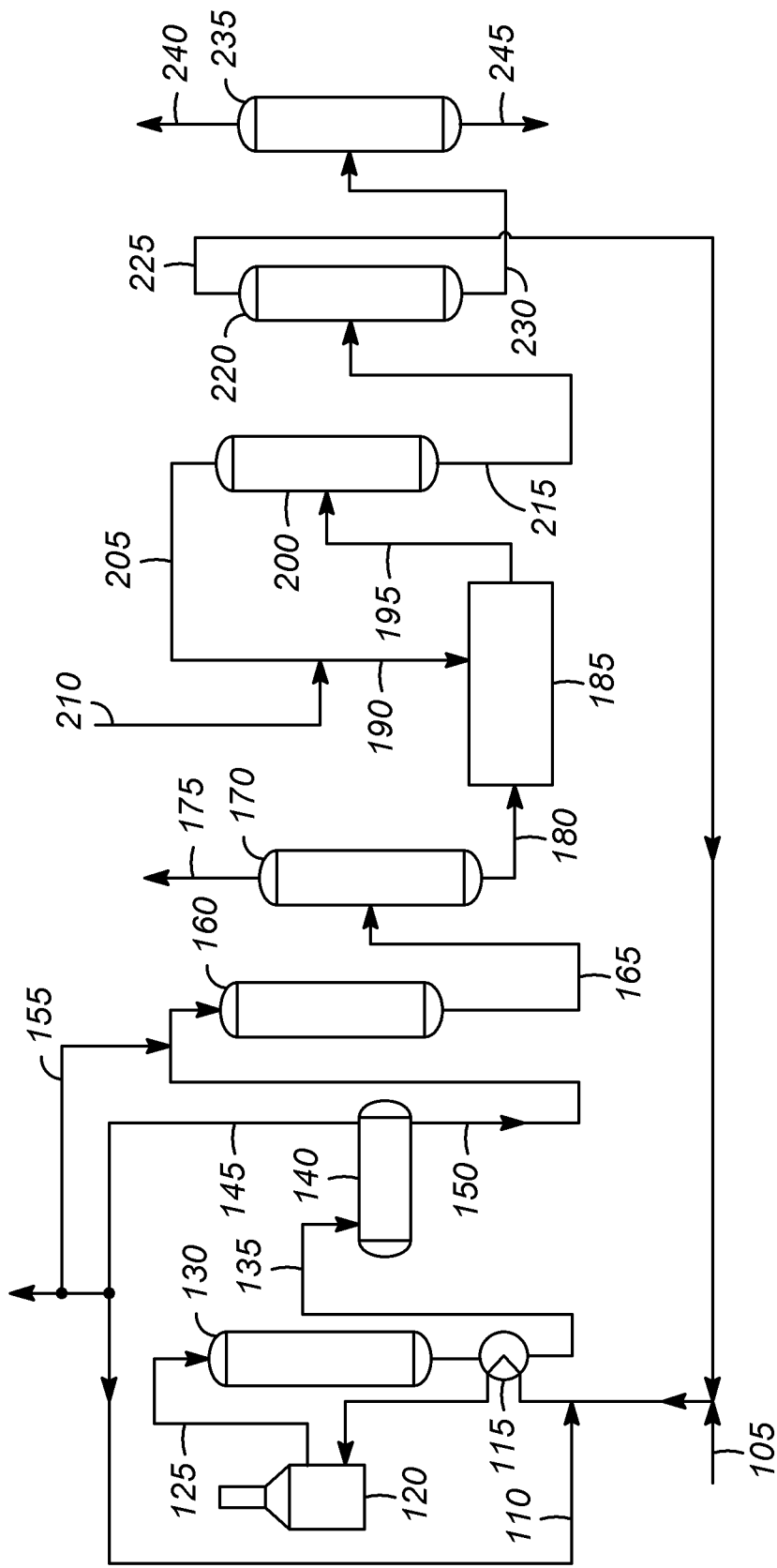
FIG. 1 is an illustration of one embodiment of an integrated process of making LAB.

Integrated processes for producing LABs using solid alkylation catalysts have been developed. One example of an integrated process is shown in FIG. 1 which includes a dehydrogenation process, followed by a selective catalytic hydrogenation process, and an alkylation process. A paraffin feed 105 is mixed with hydrogen 110 and sent through heat exchanger 115 and charge heater 120. The heated stream 125 is sent to dehydrogenation zone 130. The dehydrogenation effluent 135 exchanges heat with the feed 105 and hydrogen 110 in heat exchanger 115. The dehydrogenation effluent 135 is then sent to a separator 140 and separated into a hydrogen gas stream 145 and liquid stream 150. The liquid stream 150 is mixed with hydrogen 155 sent to a selective hydrogenation zone 160 where any diolefins are hydrogenated to monoolefins. The effluent 165 from the selective hydrogenation reactor 160 is sent to a stripper 170 where light ends 175 are removed. The bottoms stream 180 from the stripper 170 is sent to the alkylation zone 185 where it is mixed with a benzene stream 190. The effluent 195 from the alkylation zone 185 is sent to a benzene distillation column 200. The benzene overhead stream 205 can be mixed with fresh benzene 210 to form the benzene stream 190. The bottoms stream 215 from the benzene column 200 is sent to a paraffin distillation column 220. The paraffin overhead stream 225 is mixed with paraffin feed 105 and sent to the dehydrogenation zone 130. The bottoms stream 230 from the paraffin column 220 is sent to a linear alkylbenzene distillation column 235 where it is separated into an overhead stream 240 containing the linear alkybenzene and a bottoms stream 245 containing heavy alkylates. The overhead stream 240 can be further processed, for example, in a finishing column (not shown), if desired. The bottoms stream of heavy alkylates can be further processed, for example, in a transalkylation unit (not shown), to further enhance the yield of linear alkylbenzene, if desired.

The linear alkylbenzene product stream can be rated by its 2-phenyl content, and alkylbenzene sulfonates having a higher 2-phenyl content have higher solubility and viscosity in an aqueous media. The 2-phenyl content depends on the molar ratio of benzene:olefin in the reactor and requires precise control to maintain optimum product quality. A level higher or lower than the optimum range can make the LAB quality unacceptable.

Linearity is another significant property in the LAB product. Linearity is responsible for the biodegradability of the surfactant, and should be maintained as high as possible, desirably above about 90%. The linearity of LAB is highly dependent on the effluent temperature of the alkylation reaction zone. A higher temperature is detrimental to the linearity and can render the LAB unacceptable for commercial applications.

The use of feeds other than crude-based feedstocks in the alkylation process can present problems. For example, the product of the GTL process has a higher percentage of olefins (e.g., about 25% olefins and 75% paraffins) in the mixture than a feed from the Pacol™ dehydrogenation process (9-15% olefins). The alkylation of olefins and benzene is an exothermic process, and higher concentrations of olefins in the feed result in a higher exotherm which must be considered in controlling the process.

In order to address these problems, alkylation processes utilizing recycle streams have been developed.

The aromatic compound used in the alkylation process can be any suitable aromatic compound, including, but not limited to, benzene, toluene, ethylbenzene, xylenes, or combinations thereof. Benzene is the most commonly used aromatic compound. Consequently, benzene will be used for ease of discussion.

The feed will typically have a concentration of olefins between about 12 wt % and about 30 wt % and of paraffins between about 70 wt % to about 88 wt %. Within the range of about 20 wt to about 30 wt %, there is a clear optima for each olefin content, as well as sufficient energy savings to make the process economically justifiable and more attractive compared to other alternative solutions. When the concentration of olefins is below about 20%, the flow rate of the recycle stream is low, and the design loses its attractiveness as a superior configuration because it does not lead to substantial energy savings, although it is effective. Under such conditions, other exotherm control designs, such as using an additional amount of recycle benzene, or a paraffin slip-stream to act as the heat-sink may be equally applicable, depending on the specific concentration of olefins. When the concentration is above about 30%, the amount of benzene in the recycle stream relative to the recycle benzene from the benzene column is increased, making the benzene to olefin ratio in the different beds significantly different. This leads to a lack of control in the 2-phenyl content when linearity is maintained, and vice versa.

The aliphatic feedstock used in the alkylation processes of this invention contains aliphatic mono-olefin of 8 to 20, or 8 to 18, or 8 to 17 carbon atoms per molecule. The aliphatic olefin is usually a mixture of olefins having different molecular weights. The olefin may be an alpha-olefin or comprise a mixture of olefin isomers. In most instances, the positioning of the olefinic bond in the molecule is not critical as most solid alkylation catalysts have been found to promote migration of the olefinic bond.

For commercial processes, other components may be present in the aliphatic feedstock with the olefin-containing aliphatic compound. These other components may comprise paraffins of 8 to 20, or 8 to 18, or 8 to 17 carbon atoms per molecule. However, such amounts of paraffin are not critical to the processes of this invention, and aliphatic feedstocks having an essential absence of paraffins can be used. If paraffins are not present, then another component that can act a heat sink and remains unreacted under the process conditions will need to be present to maintain the LAB linearity and 2-phenyl content.

The linearity parameter is feed dependent. The drop in linearity occurs due to isomerization of olefins in the presence of the acid sites of the alkylation catalyst. As the isomerized branched olefins react with the benzene in alkylation, they make non-linear mono-alkylbenzene. As discussed more fully below, the higher the exotherm (delta T) across the catalyst bed, the higher the drop in linearity. By restricting the delta T across the catalyst bed by supplying a heat sink through the use of the recycle stream, the linearity drop can be minimized. If the feed is x % linear (i.e., x % linear olefins and 100-x % branched olefins), the drop in linearity between the olefin feed and product mono-alkylbenzene is desirably no more than about 10%.

In some embodiments, a multi-bed alkylation reaction zone and a split feedstream for controlling the 2-phenyl content in an alkylbenzene product stream are employed. This arrangement is described in U.S. Pat. No. 8,389,787, which is incorporated herein. The split-bed design of U.S. Pat. No. 8,389,787 is optimized for feedstock utilization and energy consumption. A recycle stream is added to manage the exotherm by increasing the heat sink in the reactor, while still maintaining the desired local benzene:olefin ratio in the alkylation reaction zone for optimal catalyst performance and product quality.

The local benzene to olefin molar feed ratio should be between 1 and 30, or between 10 and 25, or between 15 and 25. By local benzene to olefin molar feed ratio we mean the actual benzene to olefin molar feed ratio that is established at the reactor-bed in the presence of the catalyst. The desired local ratio is catalyst dependent. Zeolitic catalysts will have a lower requirement compared to amorphous catalysts.

The global benzene to olefin molar feed ratio should be between 2 and 20, or between 2 and 12, or between 2 and 10. By global benzene to olefin molar feed ratio we mean the molar ratio of the actual flowrate of benzene brought in the recycle benzene stream to the total olefins feed to the alkylation zone. In other words, the global ratio is a measure of the fractionation load on the benzene column. The global ratio is dependent on the process design parameters such as number of beds in a multi-bed alkylation reaction zone, and actual flow configuration.

The actual amount of benzene brought to the reactor is substantially lower compared with the existing process. However, splitting the olefin stream into multiple streams artificially increases the local benzene to olefin ratio. Therefore, lower global aromatic compound to aliphatic feedstock ratios (benzene to olefin ratios in the case of alkylbenzene) can be used, while providing an alkylated product of the desired quality. This results in savings in recovery and recycling of the aromatic compound.

The ratio of olefins to other components in the incoming feed is 0.12 to 0.3 (12-30 wt %), or 0.2 to 0.3 (20-30 wt %), as discussed above. After the recycle has been mixed with the incoming feed, the ratio typically drops below 0.2.

The aromatic compound and the olefin are reacted under alkylation conditions in the presence of a solid alkylation catalyst. These alkylation conditions generally include a temperature in the range between about 80° C. and about 200° C., most usually at a temperature not exceeding about 175° C., e.g., 100° C. to 160° C. Typically, as the catalyst ages, the temperature of the alkylation is increased to maintain desired activity. The alkylation is an exothermic reaction, and thus in a substantially adiabatic reactor, the effluent is at a higher temperature than that of the feed (Reaction Zone Delta T). A substantially adiabatic reactor is one where the increase in temperature of the effluent over that of the feed accounts for at least about 75 percent of heat generated by the reactions in the reaction zone.

Typically, the temperature within a reaction zone has been maintained within a suitable range by providing a large excess of aromatic compound to the reaction zone to absorb heat. Where the aliphatic feedstock contains paraffins, the paraffins also serve to absorb heat from the exothermic reactions. High exothermic temperatures during the alkylation can result in negative effects not only in terms of catalyst deactivation, but also in terms of product quality degradation, especially skeletal isomerization, and, in particular, skeletal isomerization of the olefin.

The ratio of aromatic compound (or preceding reaction zone effluent with respect to the subsequent reaction zones in the series) to aliphatic feedstock fed to each reaction zone in accordance with the processes of this invention is selected such that the Reaction Zone Delta T is less than about 15° C., or less than about 12° C., or less than about 10° C., or between about 2° C. to 10° C. Desirably, the amount of aliphatic feedstock to each reaction zone is such that no reaction zone has a Reaction Zone Delta T greater than about 5° C. than any other reaction zone. Desirably, the difference in the Reaction Zone Delta T among the reaction zones is less than about 5° C.

Since the alkylation is typically conducted in the presence of a liquid phase, and preferably in either an all-liquid phase or at supercritical conditions, pressures must be sufficient to maintain reactants in the liquid phase. The requisite pressure necessarily depends upon the olefin and temperature, but normally is in the range of about 1300 to 7000 kPa(g), and most usually between about 2000 and 3500 kPa(g).

In some embodiments, alkylation of benzene by the olefins is conducted in a continuous manner using three or more catalyst beds in flow series. For purposes herein, a catalyst bed is termed a reaction zone whether in the same or a separate vessel from another bed. Each reaction zone has an inlet region and an outlet region. The reactants may be in admixture prior to entering the inlet region of the reaction zone, or they may be individually introduced and mixed in the reaction zone.

The catalyst may be used as a packed bed, a moving bed, or a slurry bed. The feed to the reaction zone may be passed either upflow or downflow, or even horizontally as in a radial bed reactor; however, the flows of the aromatic compound and olefin are co-current. In one desirable variant, olefin may be fed into several discrete points within the reaction zone. The feed mixture, that is, aromatic compound and aliphatic feedstock to a reaction zone, is often provided at an overall liquid hourly space velocity (overall LHSV) between about 0.3 and about 6 or 10 hr$^{-1}$, and most frequently between about 0.4 and 6 hr$^{-1}$ depending upon, e.g., alkylation temperature and the activity of the catalyst. The overall LHSV is determined from the LHSV's of each of the beds. The reciprocal of the overall LHSV is the sum of the reciprocals of the LHSV of each of the beds in series.

It is usually desired that sufficient residence time in the reaction zone be used such that at least about 90, or at least about 95, or at least about 98, and often at least about 99.5, mass percent of the olefin fed to a reaction zone is reacted in that reaction zone.

Any suitable solid alkylation catalyst may be used in the present invention, provided that the requirements for conversion, selectivity, and activity are met. Typically, the catalysts are acidic. Preferred alkylation catalysts comprise zeolites having a zeolite framework type selected from the groups consisting of beta, MOR, MWW, FAU and NES. Suitable zeolites include mordenite, ZSM-4, ZSM-12, ZSM-20, offretite, gmelinite, beta, NU-87, UZM-8, MCM-22, MCM-36, MCM-49, zeolite Y, zeolite X, and gottardite. The MOR, MWW, FAU, NES, and other zeolite framework types are described in Ch. Baerlocher, W. M. Meier and D. H. Olson, "Atlas of Zeolite Framework Types," 5th Ed., Elsevier: Amsterdam, 2001, herein incorporated by reference. The FAU and UZM-8 molecular sieves may have any convenient particle size. Often the particle sizes of the molecular sieves range upwards of 5 microns or more in major dimension, for example, about 50 to 5000 nanometers in major dimension. Particle sizes in the lower portion of the range are sometimes preferred as the coproduction of heavies may be reduced. Major particle dimensions of less than about 500, e.g., from about 50 to 300, nanometers are often desirable. Another class of acidic, solid catalysts are acidified refractory oxides such as chlorided, fluorided, or sulfated alumina, gallia, boria, molybdia, ytterbia, titania, chromia, silica, zirconia, and the like and combinations thereof. Clays and amorphous catalysts may also find utility. Further discussion of alkylation catalysts can be found in U.S. Pat. Nos. 5,196,574; 6,315, 964B1 and 6,617,481B1.

Newer alkylation catalysts can also be used in this process. For example, one such catalyst comprises a mixture of two types of zeolitic materials, where the zeolites are mixed and produced to have two zeolites within a single catalyst pellet. With the new catalysts, the first zeolite is also characterized by its acidity, wherein the acidity is characterized by having less than 70% of $NH_3$ desorption off the zeolite at temperatures greater than 400° C. The $NH_3$-TPD experimental procedure comprises: calibration of the NH.sub.3-TPD system with 5 injections of 0.2 cc pulses of $NH_3$ at 2 minute intervals into a flow of UHP grade helium at 40 cc/minute. The data collected from the Thermal Conductivity Detector is integrated and used to calibrate the detector response to a known quantity of $NH_3$. An equilibrated sample, for moisture content is weighed at approximately 250 mg and placed in the reactor. The sample is pretreated in a flow of 20% $O_2$/He UHP grade at a rate of 100 cc/minute and with a temperature ramp of 10° C./minute up to a maximum temperature of 650° C. The sample is held at this temperature for one hour, then purged with UHP grade helium for 15 minutes and cooled to the saturation temperature. The pretreatment is for removal of water and residual contaminants. The sample is saturated with anhydrous NH.sub.3 at 150° C. using multiple pulses of $NH_3$ injected into He flowing at 40 cc/min. The minimum quantity of $NH_3$ used to saturate the sample is 50 cc. The excess ammonia is purged from the sample in flowing (40 cc/min) UHP grade helium for about 8 hours. The $NH_3$ is desorbed from the sample in a flow (40 cc/min) of UHP grade helium with a temperature ramp of 10° C/minute to a final temperature of about 605° C. All gases have been purified using appropriate gas purifiers. The $NH_3$ desorbed is detected with a Thermal Conductivity Detector. The detector response is converted to moles of $NH_3$ using the detector response obtained at the beginning of the experiment. The integrated results are reported by integration of the temperature range of interest and reported as mmoles $NH_3$/g sample. An example of the first zeolite is UZM-8.

The second zeolite having a silica to alumina molar ratio less than 8, and includes a rare earth element incorporated into the zeolitic framework in an amount greater than 16.5 wt %. The first zeolite component is in an amount between 10 and 90% by weight of the catalyst, and the second zeolite component is in an amount between 10 and 90% by weight. The zeolites are intermingled into single catalyst particles. An example of the second zeolite is a rare earth substituted X zeolite, Y zeolite, or a zeolite having an EMT/FAU intergrowth. The incorporation of rare earth exchanged ions in a low ratio zeolite reduces the acidity due to an increase in the number of framework alumina at low ratios, and also reduces geometric space in the supercage. The reduced acidity and reduced space significantly suppresses the isomerization and cracking pathways, while the leaving the primary alkylation reaction unaffected. This decreases the undesired side reactions that reduce the amount and quality of the LAB product. This is contrary to what one would expect, as it has been found that incorporating or leaving some alkali or alkaline earth cations in the catalyst significantly improves the catalyst performance. This is especially true with respect to the performance around the linearity of the alkylbenzene, and the retention of linearity as the operating temperatures are increased. Normally, the alkali or alkaline earth cations are removed because without the rare earth exchange, the alkali or alkaline earth cations are detrimental to the catalyst life and regenerability.

The same or different catalyst may be in each reaction zone of the alkylation reactor assembly.

The alkylation reaction zone may contain at least 2, or at least 3, and most frequently between about 3 and 10, reaction zones in series to which a portion of the aliphatic feedstock is fed. Often a trim alkylation reaction zone follows the series to react residual olefin in the effluent from the last reaction zone in series. The reaction zones may be in a common vessel or in separate vessels. The reaction zones may be the same or different sizes. Additional reaction zones may be used in parallel.

The number of reaction zones in series will be related to the overall aromatic compound to aliphatic feed ratio desired and to the desired Reaction Zone Delta T. For example, for a given ratio, more reaction zones will be required to achieve a given Reaction Zone Delta T than for a higher Reaction Zone Delta T.

A heat exchanger may be provided between each of the reaction zones in the series. If desired, a heat exchanger can be provided immediately upstream of any trim reaction zone, but the use of such a heat exchanger is not required. As used herein, a heat exchanger is a unit operation which provides controlled cooling of the effluent from the preceding reaction zone by direct, indirect, or a combination thereof heat exchange and does not refer to ambient heat loss. The amount of cooling to be effected between each reaction zone can be varied widely. Generally, the cooling is at least sufficient to remove at least about 75 percent of the heat generated in the preceding reaction zone. The cooled effluent is often at a temperature at least 5° C., and sometimes between 5° C. and 20° C., lower than the temperature of the effluent fed to the heat exchanger. Often the cooling is sufficient to provide the effluent at substantially the same temperature as the feed to the preceding reaction zone. In one embodiment, the cooling of the effluent is sufficient to reduce the temperature of the effluent by a least an amount of 60 percent of the Reaction Zone Delta T of the reaction zone producing the effluent. Thus, the cooling counters the Reaction Zone Delta T of the preceding reaction zone.

A portion of the aliphatic feed is fed to each of the reaction zones in the series. Advantageously, this feed can be cooler than the preceding reaction zone effluent and serves to provide direct heat exchange. Alternatively or in addition, indirect heat exchange can be used to reduce the temperature of the effluent. The cooling medium for the indirect heat exchange may be water or any conveniently available, cooler process fluid.

The optional trim reaction zone typically assures that at least about 99, preferably at least about 99.5, mole percent of the olefin is reacted. In one preferred embodiment, substantially all of the olefin contained in the zone effluent that is passed to the trim reaction zone is consumed.

The effluent from the last reaction zone (or trim reaction zone if used) is directly passed to the refining system. The alkylbenzene refining system serves to remove aromatic compound, olefins, heavies, and, if present, paraffins, from the alkylated product.

In common commercial configurations for alkylbenzene, the refining assembly comprises a distillation assembly that recovers essentially all the benzene from the alkylation effluent and provides a relatively pure benzene stream as the overhead. The bottoms stream from this distillation assembly would then be passed to a distillation assembly to separate as the overhead, paraffins and unreacted olefins, and the bottoms from this second distillation assembly would be fed to a heavies distillation assembly where the alkylbenzene product is contained in the overhead. If desired, a finishing column may be used to further purify the alkylbenzene, especially after a clay treatment to remove color formers.

In further detail for purposes of illustration, the benzene distillation is generally conducted with a bottoms temperature of less than about 300° C., preferably less than about 275° C., usually between about 230° C. and 270° C., and at a pressure at which the overhead is provided of between about 5 and 300, preferably between about 35 and 70, kPa gauge. The overhead generally contains less than about 2, preferably less than about 1.5, weight percent paraffins. The benzene distillation assembly may comprise one or more distillation columns. More than one overhead may be obtained from the benzene distillation assembly. For instance, a highly pure stream may be obtained for process needs such as regenerating catalysts or sorbents, e.g., having a paraffin concentration less than about 1, preferably less than about 0.1, weight percent. A lesser purity overhead may be obtained from the benzene distillation assembly, e.g., as a side draw, for use as a recycle to the alkylation reaction.

Each column used for benzene distillation may contain any convenient packing or distillation trays, but most often trays such as sieve and bubble trays, are used. Often the assembly provides at least about 5 theoretical plates, for example, 6 to 70, or 20 to 50. The reflux ratio is often in the range of about 2:1 to 1:10, or about 1.5:1 to 1:5. The bottoms stream from the benzene distillation generally contains less than about 1000 ppmw, or less than about 50 ppmw, and sometimes less than about 5 ppmw, benzene. The benzene distillation may occur in a single column or two or more distinct columns may be used. For instance, a stripping column may be used to remove a portion, e.g., 20 to 50 percent, of the benzene and then the bottoms from the stripping column would be subjected to rectification in a subsequent column to obtain the desired separation.

The paraffin distillation is generally conducted with a bottoms temperature of less than about 300° C., or less than about 275° C., usually between about 250° C. and 275° C., and at a pressure at which overhead is provided of between about 5 and 110 kPa absolute, or between about 10 and 50 kPa absolute. The column may contain any convenient packing or distillation trays, but most often sieve trays are used. Often the paraffins distillation assembly provides at least about 5 theoretical plates, or about 7 to about 20. The reflux ratio is often in the range of about 3:1 to 1:10, or about 1:1 to 1:3. The bottoms stream from the paraffins distillation generally contains less than about 5000, or less than about 500, parts by million by weight (ppmw) paraffins and less than about 10, often less than about 1, ppmw benzene. The paraffins distillation may occur in a single column, or two or more distinct columns may be used.

The heavy alkylate distillation is generally conducted with a bottoms temperature of less than about 300° C., or less than about 275° C., usually between about 250° C. and 275° C., and at a pressure of between about 0.5 and 30 kPa absolute, or between about 1 and 5 kPa absolute. The column may contain any convenient packing or distillation trays, but most often structured packing is used. Often the heavy alkylate distillation assembly provides at least about 5 theoretical plates, for example 10 to 30, or 10 to 20. The reflux ratio is often in the range of about 2:1 to 1:5, or about 0.2:1 to 1:1. The overhead from the heavy alkylate distillation generally contains less than about 1000, or less than about 100 ppmw, and sometimes less than about 50 ppmw, total heavies.

The refining system may contain additional distillation zones, e.g., to recover additional alkylbenzene from heavies.

In one separation step, an aromatic-rich fraction is separated from a substantially aromatic compound-free fraction. By aromatic-rich fraction, we mean that there is at least about 95 wt % aromatic compounds, or at least about 97 wt %, or at least about 99 wt %, or at least about 99.9 wt %. By substantially aromatic compound-free fraction, we mean there is less than about 5 wt % aromatic compounds, or less than about 3 wt %, or less than about 1 wt %, or less than about 0.1 wt %.

In another separation step, the substantially aromatic-free fraction is separated into an other component-rich fraction containing the unreacted other components and a substantially other component-free fraction containing the alkylaromatics, and dialkylaromatics. By other component-rich fraction, we mean that there is at least about 95 wt % unreacted other components, or at least about 97 wt %, or at least about 99 wt %, or at least about 99.9 wt %. By substantially other component-free fraction, we mean there is less than about 5 wt % unreacted other components, or less than about 3 wt %, or less than about 1 wt %, or less than about 0.1 wt %.

In another separation step, the substantially other component-free fraction is separated into a monoalkylaromatic fraction containing the linear monoalkylaromatics and a heavies fraction containing the dialkylaromatics. The monoalkylaromatic fraction contains at least about 95 wt % monoalkylaromatics, or at least about 97 wt %, or at least about 99 wt %, or at least about 99.9 wt %. The heavies fraction contains less about 15 wt % monoalkylaromatics, or less about 10 wt %, or less about 5 wt %, or at least about 1 wt %.

Figure 2:
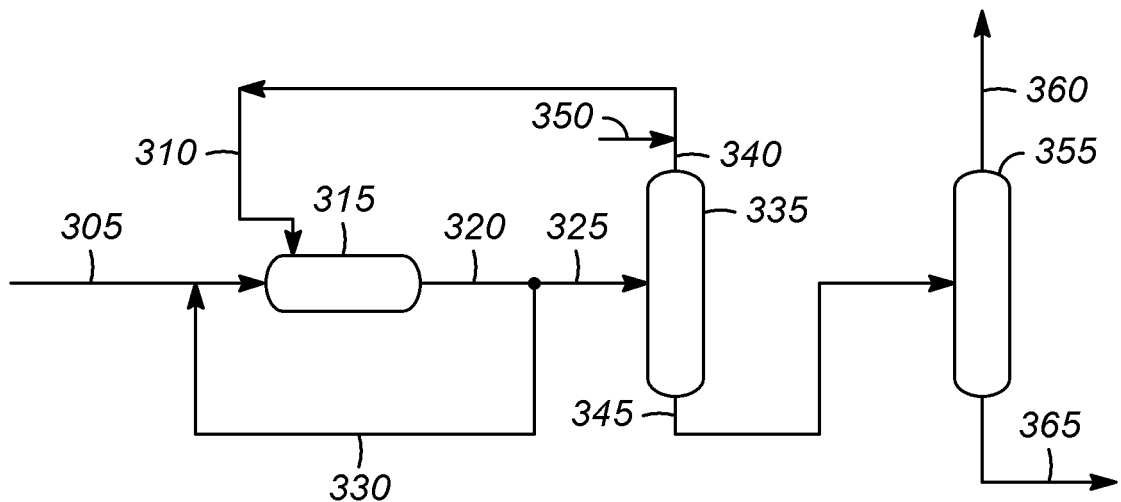
FIG. 2 is an illustration of one embodiment of a process of making LAB according to the present invention.

One embodiment of the process is shown in FIG. 2. The GTL feed 305 is sent to alkylation reaction zone 315 along with a benzene stream 310. The alkylation effluent 320 is split into a product portion 325 and a recycle portion 330. Recycle portion 330 is mixed with the GTL feed 305 and sent to the alkylation zone along with benzene stream 310. The product portion 325 is sent to benzene distillation column 335 to be separated into benzene overhead stream 340 and the bottoms stream 345. The benzene overhead stream 340 can be combined with a fresh benzene stream 350 to form benzene stream 310. The bottoms stream 345 is sent to the paraffin distillation column 355 where it is separated into the paraffin overhead stream 360 and the bottoms stream 365. The bottoms stream 365 is sent to the linear alkylbenzene distillation column (not shown).

Recycling a portion of the reaction zone effluent to back into the reaction zone lowers the exotherm. If only benzene were recycled without any effluent recycle, the amount of 2-phenyl in the product would be significantly less than the commercial solid-bed alkylation product. If only paraffin were recycled without any effluent recycle, the LAB product would be obtained, but the cost would be significantly higher because of the added fractionation cost in the benzene and paraffin columns. Recycling a portion of the reactor effluent containing both benzene and paraffins substantially reduces the amount of recycle benzene needed to maintain the benzene:olefin ratio for optimum product quality because the benzene in the effluent supplements the recycled benzene. The paraffin in the effluent provides an unreactive heat-sink without incurring the added fractionation cost in the benzene and paraffin columns. The effluent recycle process significantly reduces the fractionation load needed to maintain LAB product quality.

Figure 3:
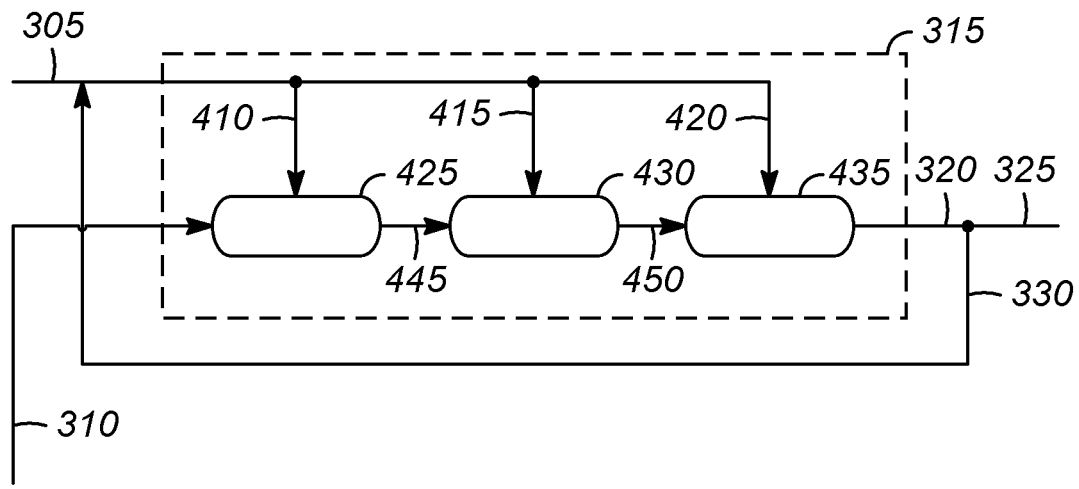
FIG. 3 is an illustration of one embodiment of a reactor zone in the process shown in FIG. 2.

FIG. 3 shows one embodiment of a split bed alkylation reaction zone 315 that can be used in the process. The GTL feed 305 is mixed with recycle portion 330 and split into three feed portions 410, 415, 420. The 3 portions of GTL feed 410, 415, 420 are sent to three alkylation reactors 425, 430, 435. The benzene stream 310 is sent to the first alkylation reactor 425 to be reacted with the first feed portion 410. The effluent 445 from the first alkylation reactor 425 is sent to the second alkylation reactor 430 to be reacted with the second feed portion 415. The effluent 450 from the second alkylation reactor 430 is sent to the third alkylation reactor 435 to be reacted with the third feed portion 420. The effluent 320 from the third alkylation reactor 435 is split into the product portion 325 which is sent to the benzene column (not shown) and a recycle portion 330 which is recycled and added to the GTL feed stream 305.

EXAMPLE

The GTL feed 305 contains 100 paraffins and 32 olefins by weight. The system uses a three-bed reactor system with solid bed zeolitic Detal catalyst. As the olefin content of this feed is about 25%, additional heat sink is required to maintain the linearity of the linear alkylbenzene product. If additional benzene is used to provide heat-sink, the 2-phenyl content in the product is significantly lower. If a portion of the paraffin is recycled to provide the heat sink, additional fractionation and circulation costs are required. By recycling a portion of the reactor effluent, a significantly lower global benzene to olefin molar ratio of 4.25 provides appropriate benzene to olefin ratio in all three reactors. The benzene stream 310 contains 64.87 benzene. The recycle portion 330 contains 122.3 paraffins and 61.6 benzene. After the GTL feed 305 and recycle portion 330 are mixed, the feed contains 222.3 paraffins, 32 olefins, and 61.6 benzene. The molar benzene to olefin ratio of the mixed feed is 4.04. The local benzene to olefin ratio in the first alkylation reactor 425 is 17, in the second alkylation reactor 430 is 20, and in the third alkylation reactor 435 is 23.

For a 3-split-bed reactor without the present invention, the local benzene to olefin ratio is maintained at about 20 and the global ratio is about 7. An additional paraffin slip-stream from stream 360 will also be needed to control the exotherm. For the same reactor using the present invention, the local ratio will be about 20, but the global ratio is 4.25, which is about a one third reduction in the benzene column fractionation load. Also, no paraffin slip-stream is needed, leading to about 50% reduction in paraffin column fractionation load.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for preparing linear alkylbenzenes by the alkylation of benzene with olefins having between about 8 and 20 carbon atoms comprising:

contacting benzene and an effluent from a gas-to-liquid process comprising a mixture of about 12 to about 30 wt % olefins and about 70 to about 88 wt % paraffins in an alkylation zone under alkylation conditions including a catalytically effective amount of a catalyst comprising a first zeolite comprising UZM-8 and a second zeolite comprising a rare-earth substituted X or Y zeolite intermingled into single catalyst particles to provide an alkylation product containing monoalkylbenzenes, dialkylbenzenes, unreacted benzene, and unreacted paraffins;

dividing the alkylation product into a first portion and a second portion;

recycling the first portion of the alkylation product to the alkylation zone so that after the first portion of the alkylation product is mixed with the incoming feed, the ratio of olefins to the paraffins drops below 0.2;

separating the second portion of the alkylation product into a benzene-rich fraction containing the unreacted benzene and a substantially benzene-free fraction containing alkylbenzenes, unreacted paraffins, and dialkylbenzenes;

separating the substantially benzene-free fraction into a paraffin-rich fraction containing the unreacted paraffins and a substantially paraffin-free fraction containing the monoalkylbenzenes, and dialkylbenzenes;

separating the substantially paraffin-free fraction into an monoalkylbenzene fraction containing the linear monoalkylbenzenes and a heavies fraction containing the dialkylbenzenes; and controlling a ratio of the first portion of the alkylation product to the second portion of the alkylation product to obtain a specified 2-phenyl content of the linear monoalkylbenzene product; wherein the drop in linearity between the olefin feed and product monoalkylbenzene is no more than about 10%.

2. The process of claim 1 further comprising subjecting at least a portion of the heavies fraction to transalkylation conditions including a catalytically effective amount of transalkylation catalyst and benzene to provide a transalkylation product containing monoalkylbenzenes, unreacted dialkylbenzenes, and unreacted benzene.

3. The process of claim 1 further comprising recycling at least a portion of the benzene-rich fraction to the alkylation zone.

4. The process of claim 1 wherein a global mole ratio of benzene to olefin supplied to the alkylation zone is in a range of about 2 to about 20.

5. The process of claim 1 wherein a temperature of the alkylation product exiting the alkylation zone is in a range of about 100° C. to about 160° C.

6. The process of claim 1 wherein the alkylation zone comprises at least two alkylation zones and further comprising periodically regenerating the catalyst in at least one of the alkylation zones by continuously passing benzene through the at least one alkylation zone under regeneration conditions to provide a spent benzene stream containing deactivating components.

7. The process of claim 1 wherein the ratio of the first portion of the alkylation product to the second portion of the alkylation product is between about 0.5 and about 2.5.

8. The process of claim 1, wherein the paraffins having between about 8 and 20 carbons.

\* \* \* \* \*